US008759609B2

(12) United States Patent
Cai et al.

(10) Patent No.: US 8,759,609 B2
(45) Date of Patent: Jun. 24, 2014

(54) METHODS FOR CORN TRANSFORMATION (75) Inventors: Tishu Cai, Ellisville, MO (US); Shubha Subbarao, Ballwin, MO (US); Yuechun Wan, Madison, WI (US); Richard A. Yingling, Chesterfield, MO (US); Michael T. Mann, Groton, CT (US); Anita Otal, Wildwood, MO (US); David D. Songstad, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 180 days.

(21) Appl. No.: 12/729,072

(22) Filed: Mar. 22, 2010

(65) Prior Publication Data

US 2010/0235942 A1    Sep. 16, 2010

Related U.S. Application Data (62) Division of application No. 10/709,826, filed on Jun. 1, 2004, now Pat. No. 7,682,829.

(60) Provisional application No. 60/474,589, filed on May 30, 2003.

(51) Int. Cl.
*C07K 14/415* (2006.01)
*A01H 5/10* (2006.01)
*A01H 1/02* (2006.01)

(52) U.S. Cl.
USPC ........ 800/278; 800/294; 800/288; 800/300.1; 800/268; 800/320.1

(58) Field of Classification Search
None
See application file for complete search history.

(56) References Cited

U.S. PATENT DOCUMENTS

| | | | |
|---|---|---|---|
| 5,986,173 A | 11/1999 | Smeekens et al. | |
| 6,329,571 B1 | 12/2001 | Hiei | |
| 7,682,829 B2 * | 3/2010 | Cai et al. | 435/469 |
| 2004/0210958 A1 | 10/2004 | Duncan et al. | |
| 2004/0244075 A1 | 12/2004 | Cai et al. | |
| 2005/0138693 A1 | 6/2005 | Duncan | |
| 2008/0118981 A1 | 5/2008 | Akula et al. | |
| 2008/0124727 A1 | 5/2008 | Rout et al. | |

OTHER PUBLICATIONS

Frame et al. 2002, Plant Physiology 129:13-22.*
Hansen et. al., 1999, Trends in plant Science, vol. 4, pp. 226-231.*
Cheng et al., "Genetic transformation of wheat mediated by agrobacterium tumefaciens," *Plant Physiol.*, 115:971-980, 1997.
Frame et al., "*Agrobacterium tumefaciens*-mediated transformation of maize embryos using a standard binary vector system," *Plant Physiol.*, 129:13-22, 2002.
Hansen et al., "Recent advances in the transformation of plants," *Trends in Plant Sci.*, 4:226-231, 1999.
Hiei et al., "Agrobacterium-mediated transformation of rice using immature embryos of calli induced from mature seed," *Nature Protocols*, 3(5):824-834, 2008.
Kramer et al., "Selection of transformed protoplast-derived *Zea mays* colonies with phosphinothricin and a novel assay using the pH indicator chlorophenol red," *Planta*, 190:454-458, 1993.
Roy et al., "Production of agronomically superior transgenic rice plants using agrobacterium transformation methods: present status and future perspectives," *Current Science*, 79(7):954-960, 2000.
Sheridan, "Tissue Culture of maize I. callus induction and growth," *Phsiologia Plantarum*, 33(2):151-156, 1975 (abstract only).
Tisserat, "Embryogenesis, organogenesis and plant regeneration," In: Plant Cell Culture—A Practical Approach, Dixon (Ed.), IRL Press, Oxford, pp. 79-90, 1985.
Toki, "Rapid and efficient agrobacterium-mediated transformation in rice," *Plant Mol. Biol. Reporter*, 15(1):16-21, 1997.
Zhao et al., "High throughput genetic transformation mediated by *Agrobacterium tumefaciens* in maize," *Mol. Breed.*, 8:323-333, 2001.

* cited by examiner

*Primary Examiner* — Brent T Page
*Assistant Examiner* — Jared Shapiro
(74) *Attorney, Agent, or Firm* — Dentons US LLP; Thomas P. McBride; David J. Lanzotti (57) ABSTRACT The present invention relates to a novel transformation system for generating transformed corn plants. In particular, the invention relates to a rapid selection system at an elevated temperature that allows faster and more efficient transformation.

8 Claims, 3 Drawing Sheets

METHODS FOR CORN TRANSFORMATION

This application is a divisional of U.S. application Ser. No. 10/709,826, now U.S. Pat. No. 7,682,829, filed Jun. 1, 2004, the disclosure of which is incorporated herein by reference in its entirety, which application claims priority to U.S. Provisional Application 60/474,589, filed May 30, 2003, herein incorporated by reference in its entirety.

BACKGROUND OF INVENTION

The present invention relates to the field of plant biotechnology. More specifically, it concerns methods for incorporating genetic components into a plant via genetic engineering techniques. In particular, provided herein are systems for genetically transforming corn.

During the past decade, it has become possible to transfer genes from a wide range of organisms to crop plants by recombinant DNA technology. This advance has provided enormous opportunities to improve plant resistance to pests, disease and herbicides, and to modify biosynthetic processes to change the quality of plant products for food, feed and industrial uses.

*Agrobacterium*-mediated transformation is one method for introducing a desired genetic element into a plant and is achieved through the use of a genetically engineered soil bacterium belonging to the genus *Agrobacterium*. Several *Agrobacterium* species mediate the transfer of a specific DNA known as "T-DNA" that can be genetically engineered to carry a desired piece of DNA into many plant species. The major events marking the process of T-DNA mediated pathogenesis are induction of virulence genes, processing and transfer of T-DNA.

*Agrobacterium*-mediated genetic transformation of plants involves several steps. The first step, in which the virulent *Agrobacterium* and plant cells are first brought into contact with each other, is generally called "inoculation". Following the inoculation step, the *Agrobacterium* and plant cells/tissues are usually grown together for a period of several hours to several days or more under conditions suitable for growth and T-DNA transfer. This step is termed "co-culture". Following co-culture and T-DNA delivery, the plant cells are often treated with bactericidal or bacteriostatic agents to kill the *Agrobacterium*. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps. Both the "delay" and "selection" steps typically include bactericidal or bacteriostatic agents to kill any remaining *Agrobacterium* cells because the growth of *Agrobacterium* cells is undesirable after the infection (inoculation and co-culture) process.

Another widely used technique to genetically transform plants involves the use of microprojectile bombardment. In this process, a nucleic acid containing the desired genetic elements to be introduced into the plant is deposited on small metallic, e.g., gold or tungsten, particles, which are then delivered at a high velocity into the plant tissue or plant cells. Cells containing the desired genetic elements are then placed in tissue culture and transformed cells selected through the use of one or more selection system that has been incorporated into the genetic elements transformed into the plant.

The major deficiencies in current plant transformation systems include but are not limited to the production efficiency of the system, and transformation variability due to genotype or species diversity and explant limitations. In particular, there is a continuing need in the field of plant biotechnology to provide more efficient transformation methods suitable for high capacity production of economically important plants, particularly elite cultivars.

SUMMARY OF INVENTION

The present invention provides novel methods for the stable and efficient transformation of cereal plants, particularly corn (maize or *Zea mays*) plants, under selection conditions that enable a rapid and efficient transformation process.

In one aspect, the present invention provides a method of transforming corn plants by introducing into transformable corn tissue via a biotechnological transformation process a nucleic acid sequence containing at least one genetic component containing a selectable marker nucleic acid that provides a means for selecting corn tissue containing the genetic component from those not containing the genetic component, and subjecting the transformed corn tissue to tissue culture media containing a selection agent corresponding to the selectable marker nucleic acid at an elevated temperature for a period of time sufficient to identify and select transformed plants (or tissue) containing the desired genetic component.

Still another aspect of the present invention relates to a method for transforming corn tissue with a genetic component containing at least one selectable marker nucleic acid and subjecting the transformed tissue to a tissue culture media containing the corresponding selection agent for a period of not more than twenty-one days and identifying and selecting transformed corn tissue containing the desired genetic component for regeneration into a fertile, transgenic plant.

In a still further aspect of the present invention, the selection step is conducted in a single tissue culture media vessel containing the selective agent, and the tissue surviving selection is immediately transferred to a regeneration media for development into fertile, transgenic maize plants.

In another aspect of the present invention, the transformable corn tissue is transformed via *Agrobacterium*-mediated transformation methods wherein the exposure of the corn tissue to the *Agrobacterium* is minimized, it is inoculated by methods that limit its exposure to anerobiosis conditions during the *Agrobacterium* inoculation. Various means for minimizing exposure may be utilized including limiting the time of submersion in the *Agrobacterium* solution, inoculating with a small drop of *Agrobacterium* solution, and inoculating with filter paper saturated with the *Agrobacterium* solution.

Yet another aspect of the present invention relates to any seeds, or progeny including hybrid combinations of the transformed plants produced by the methods of the present invention.

Further objects, advantages and aspects of the present invention will become apparent from the accompanying figures and following description of the invention.

DETAILED DESCRIPTION

The present invention is particularly directed to the transformation of any cereal plant, particularly corn lines. The present invention provides for a rapid and efficient process for obtaining transformed corn plants by reducing the time the transformable explants spend in the selection phase, which in this system is the callus induction phase, of a typical transformation process and by increasing the temperature during the selection phase. It has been discovered that placing the transformed corn explant on a tissue culture media containing a selective agent for a total period of 2-4 weeks is sufficient to select for transformed plants and to obtain fertile transgenic plants therefrom. Moreover, the transformed explants may be placed in a single vessel containing the selection media for the entirety of the selection period with efficacious results, thus eliminating the need for repeated subculturing and transfer of the explants to fresh media. In this method, it is often desirable to maintain selection pressure during the regeneration phase as well.

It has further been discovered that the transformation efficiency may be increased about twofold by maintaining the temperature during the selection phase, or at least a portion of the selection phase, at a temperature greater than 27° C., a typical corn tissue culture temperature. Preferably, the selection temperature is maintained between about 28.5° C. and about 35° C., more preferably the temperature is maintained between about 30° C. and about 34° C., and most preferably the temperature is maintained between about 30° C. and about 32° C. This elevated temperature is maintained for a period of not more than three weeks and more preferably not more than two weeks during the selection phase.

It has also been discovered that limiting the amount of submersion during *Agrobacterium* inoculation of the transformable explants increases the transformation frequency. The explants can be isolated directly into inoculation medium and then removed from the medium within 20 minutes. Explants could also be isolated into co-culture medium and then spotted with 1 µL of *Agrobacterium* solution or contacted with filter paper saturated with *Agrobacterium* solution for 5 to 60 minutes. It is believed that the anaerobiosis of being in solution is detrimental to the explants. Thus limiting or eliminating the anaerobiosis increases the transformation efficiency. It has been observed that immersion in the inoculation medium for more than 60 minutes has a detrimental effect on the explant. Thus eliminating the anaerobiosis by altering the manner or the time in which the *Agrobacterium* contacts the explant increases the transformation efficiency.

Cereal plants include monocotyledonous plants such as wheat, rice, barley, oats, sorghum, and maize.

Transformation efficiency or transformation frequency is the percentage of transformants produced from the starting explants. The present invention is directed to methods that increase the number of transformants produced from a given number of explants.

The present invention involves the delivery of a desired nucleic acid, a gene of interest, into the genome of a corn cell and the production of a fertile transgenic plant therefrom. The method of delivery of the nucleic acid is not critical to the methods of this invention and known delivery methods such as *Agrobacterium*-mediated delivery and microprojectile delivery methods may be used. Thus, in one aspect, the present invention encompasses the use of bacterial strains to introduce one or more genetic components into plants. Those of skill in the art would recognize the utility of *Agrobacterium*-mediated transformation methods. A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis, respectfully, which are used as the vectors and contain the genes of interest that are subsequently introduced into plants. Preferred strains would include but are not limited to *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

With respect to microprojectile bombardment (U.S. Pat. No. 5,550,318; U.S. Pat. No. 5,538,880; U.S. Pat. No. 5,610,042; each of which is specifically incorporated herein by reference in its entirety), particles are coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules that comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one that is capable of being used to transform a target cell, in that the transforming DNA will be delivered to the target cell, yet will be accessible to the target cell such that transformation may occur.

Any technique for coating microprojectiles that allows for delivery of transforming DNA to the target cells may be used.

Methods for coating microprojectiles that have been demonstrated to work well with the current invention have been specifically disclosed herein. DNA may be bound to microprojectile particles using alternative techniques, however. For example, particles may be coated with streptavidin and DNA end-labeled with long chain thiol cleavable biotinylated nucleotide chains. The DNA adheres to the particles due to the streptavidin-biotin interaction but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed that the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It further is contemplated that the grade of helium may affect transformation efficiency. One also may optimize the trauma reduction factors (TRFs) by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation.

The present invention can be used with any transformable plant tissue, including cells. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves. Preferably, immature embryos are used as the explant of choice.

In an embodiment of the present invention, immature embryos (IEs) of corn are used as explants for *Agrobacterium*-mediated transformation. Corn ears are harvested approximately 6-16 days after pollination and used as a source of immature embryos. The present invention thus encompasses the use of freshly isolated embryos as described.

Any suitable plant culture medium can be used. Examples of suitable media would include but are not limited to MS-based media (Mursahige and Skoog, Physiol. Plant, 15:473-497, 1962) or N6-based media (Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, such as a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Murashige and Skoog, Physiol. Plant, 15:473-497, 1962), N6 (Chu et al., Scientia Sinica 18:659, 1975), Linsmaier and Skoog (Linsmaier and Skoog, Physio. Plant., 18: 100, 1965), Uchimiya and Murashige (Uchimiya and Murashige, Plant Physiol. 15:473, 1962), Gamborg's B5 media (Gamborg et al., Exp. Cell Res., 50:151, 1968), D medium (Duncan et al., Planta, 165:322-332, 1985), McCown's Woody plant media (McCown and Lloyd, HortScience 16:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures that can be optimized for the particular variety of interest.

Once the transformable plant tissue is isolated, the plant cells in the tissue are transformed, and independently transformed plant cells are selected. The independent transformants are referred to as transgenic events.

Those of skill in the art are aware of the typical steps in the plant—*Agrobacterium*-mediated transformation process. The *Agrobacterium* can be prepared either by inoculating a liquid such as Luria Burtani (LB) media directly from a glycerol stock or streaking the *Agrobacterium* onto a solidified media from a glycerol stock, allowing the bacteria to grow under the appropriate selective conditions, generally from about 26° C.-30° C., or about 28° C., and taking a single colony or a small loop of—*Agrobacterium* from the plate and inoculating a liquid culture medium containing the selective agents. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected.

Typically, an *Agrobacterium* culture is inoculated from a streaked plate or glycerol stock and is grown overnight and the bacterial cells are washed and resuspended in a culture medium suitable for inoculation of the explant. Suitable inoculation media for the present invention include, but are not limited to ½MS PL or ½MS VI (Table 1).

The next stage of the *Agrobacterium* mediated transformation process is the inoculation. In this stage the explants and *Agrobacterium* cell suspensions are mixed together. In the present invention, immature embryos are isolated directly into the inoculation medium containing the *Agrobacterium*. Embryos are cultured in inoculation media for less than 30 min. The inoculation is generally performed at a temperature of about 15° C. to 30° C., or about 23° C. to 28° C. The inoculation can also be done by isolating the immature embryos directly onto the co-culture medium (described below) and then spotting 1 μL of *Agrobacterium* solution onto the embryo or alternatively placing a piece of filter paper saturated in *Agrobacterium* solution over the top of the embryos for about 5 to 60 minutes. The filter paper and any excess solution are then removed before co-culture.

After inoculation, any excess *Agrobacterium* suspension can be removed and the *Agrobacterium* and target plant material are co-cultured. The co-culture refers to the time post-inoculation and prior to transfer to a delay or selection medium. Any number of plant tissue culture media can be used for the co-culture step. For the present invention a reduced salt media such as ½MS-based co-culture media (Table 1) is used and the media lacks complex media additives including but not limited to undefined additives such as casein hydrolysate, and B5 vitamins and organic additives. Plant tissues after inoculation with *Agrobacterium* can be cultured in a liquid media. More preferably, plant tissues after inoculation with *Agrobacterium* are cultured on a semi-solid culture medium solidified with a gelling agent such as agarose, or a low EEO agarose. The co-culture is typically performed for about one to three days or for less than 24 hours at a temperature of about 18° C. to 30° C., or about 20° C. to 25° C. The co-culture can be performed in the light or in light-limiting conditions. Usually, the co-culture is performed in light-limiting conditions. By light-limiting conditions as used herein is meant any conditions that limit light during the co-culture period including but not limited to covering a culture dish containing the plant and *Agrobacterium* mixture with a cloth, foil, or placing the culture dishes in a black bag, or placing the cultured cells in a dark room. Lighting conditions can be optimized for each plant system as is known to those of skill in the art.

After co-culture with *Agrobacterium* or after bombardment with the microprojectile, the explants can be placed directly onto selective media. Previously, explants were sub-cultured onto selective media in successive steps or stages for 8 weeks or more. For example, the first selective media could contain a low amount of selective agent, and the next sub-culture could contain a higher concentration of selective agent or vice versa. The explants could also be placed directly on a fixed concentration of selective agent and then subcultured repeatedly to maximize selection. Alternatively, after co-culture with *Agrobacterium* or immediately after bombardment, the explants could be placed on media without the selective agent, or delay media, followed by selection as above. All of these steps took a great deal of time, resulting in prolonged culture duration. In the present invention, it has been discovered that selection of transformed corn cells can take place much faster than was previously believed. Explants (regardless of transformation method) are placed on selective media for from about 7 to about 42 days, or from about 7 to about 30 days, or from about 7 to about 21 days, or from about 7 to about 14 days. This limits the time in culture and eliminates several transfer steps, which makes the process more efficient. As previously noted, further improvement in obtained by selecting under an elevated temperature. Thus, in at least one embodiment of the invention, transformed corn explants are placed on a selection media at elevated temperature for a period of 2 weeks and then maintained for a further 1-2 weeks in the same selection media and in the same vessel at a temperature of 27° C. or below.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Additional appropriate media components can be added to the selection or delay medium to inhibit *Agrobacterium* growth. Such media components can include, but are not limited to, antibiotics such as carbenicillin or cefotaxime. The cultures are subsequently transferred to a media suitable for the recovery of transformed plantlets. Those of skill in the art are aware of the number of methods to recover transformed plants. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

To initiate a transformation process in accordance with the present invention, it is first necessary to select genetic components to be inserted into the plant tissue. Genetic components can include any nucleic acid that is introduced into a plant tissue using the method according to the invention. Genetic components can include non-plant DNA, plant DNA or synthetic DNA.

In a preferred embodiment, the genetic components are incorporated into a DNA composition such as a recombinant, double-stranded plasmid or vector molecule comprising at least one or more of following types of genetic components: (a) a promoter that functions in plant cells to cause the production of an RNA sequence, (b) a structural DNA sequence that causes the production of an RNA sequence that encodes a product of agronomic utility, and (c) a 3' non-translated DNA sequence that functions in plant cells to cause the addition of polyadenylated nucleotides to the 3' end of the RNA sequence.

The vector may contain a number of genetic components to facilitate transformation of the plant tissue and regulate expression of the desired gene(s). In one preferred embodiment, the genetic components are oriented so as to express a mRNA, that in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include but are not limited to the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). All of these promoters have been used to create various types of DNA constructs that have been expressed in plants.

Promoter hybrids can also be constructed to enhance transcriptional activity, or to combine desired transcriptional activity, inducibility and tissue specificity or developmental specificity. Promoters that function in plants include but are not limited to promoters that are inducible, viral, synthetic, constitutive, and temporally regulated, spatially regulated, and spatio-temporally regulated. Other promoters that are tissue-enhanced, tissue-specific, or developmentally regulated are also known in the art and envisioned to have utility in the practice of this invention. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (Science, 236:1299, 1987).

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes. Other genetic components that serve to enhance expression or affect transcription or translational of a gene are also envisioned as genetic components. The 3' non-translated region of the chimeric constructs should contain a transcriptional terminator, or an element having equivalent function, and a polyadenylation signal that functions in plants to cause the addition of polyadenylatednucleotides to the 3' end of the RNA. Examples of suitable 3' regions are (1) the 3' transcribed, non-translated regions containing the polyadenylation signal of—*Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 385 962).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one embodiment, the vector contains a selectable, screenable, or scoreable marker gene. These genetic components are also referred to herein as functional genetic components, as they produce a product that serves a function in the identification of a transformed plant, or a product of agronomic utility. The DNA that serves as a selection device functions in a regenerable plant tissue to produce a compound that confers upon the transformed plant tissue resistance to an otherwise toxic compound when exposed to the compound in tissue culture media or in other media, including soil. Genes that may usefully be used as a selectable, screenable, or scorable marker include but are not limited to GUS, green fluorescent protein (GFP), luciferase (LUX), antibiotics like kanamycin (Dekeyser et al., Plant Physiol., 90:217-223, 1989), and herbicides like glyphosate (EPSPS, Della-Cioppa et al., Bio/Technology, 5:579-584, 1987), dalapon (deh), bromoxynil (bxn), sulfonyl herbicides (ALS, GST-II), bialaphos (bar), atrazine, (GST-III). Other selection devices can also be implemented including but not limited to tolerance to phosphinothricin, bialaphos, and positive selection mechanisms (Joersbo et al., Mol. Breed., 4:111-117, 1998)

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for insect or pest tolerance, herbicide tolerance, genes for quality improvements such as yield, nutritional enhancements, environmental or stress tolerances, or any desirable changes in plant physiology, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech Gen. Engin. Rev., 9:207-227, 1991). The RNA could also be a catalytic RNA molecule (i.e., a ribozyme) engineered to cleave a desired endogenous mRNA product (see for example, Gibson and Shillitoe, Mol. Biotech. 7:125-137, 1997). More particularly, for a description of anti-sense regulation of gene expression in plant cells see U.S. Pat. No. 5,107,065 and for a description of RNAi gene suppression in plants by transcription of a dsRNA see U.S. Pat. No. 6,506,559, U.S. Patent Application Publication No. 2002/0168707

A1, and U.S. patent application Ser. No. 09/423,143 (see WO 98/53083), Ser. No. 09/127,735 (see WO 99/53050) and Ser. No. 09/084,942 (see WO 99/61631), all of which are incorporated herein by reference. Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term exogenous is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable and/or screenable marker genes, regulatory elements, and other sequences of interest will be apparent to those of skill in the art. Therefore, the foregoing discussion is intended to be exemplary rather than exhaustive.

After the construction of the plant transformation vector or construct, said nucleic acid molecule, prepared as a DNA composition in vitro Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Bacterial Strains and Plasmids

Figure 1:
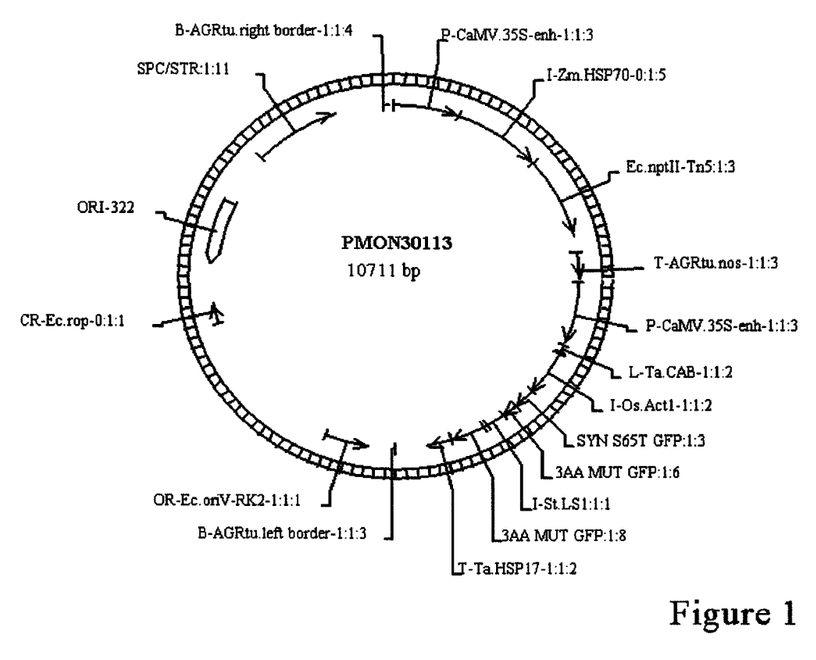
FIG. 1 is a plasmid map of pMON30113.
Figure 2:
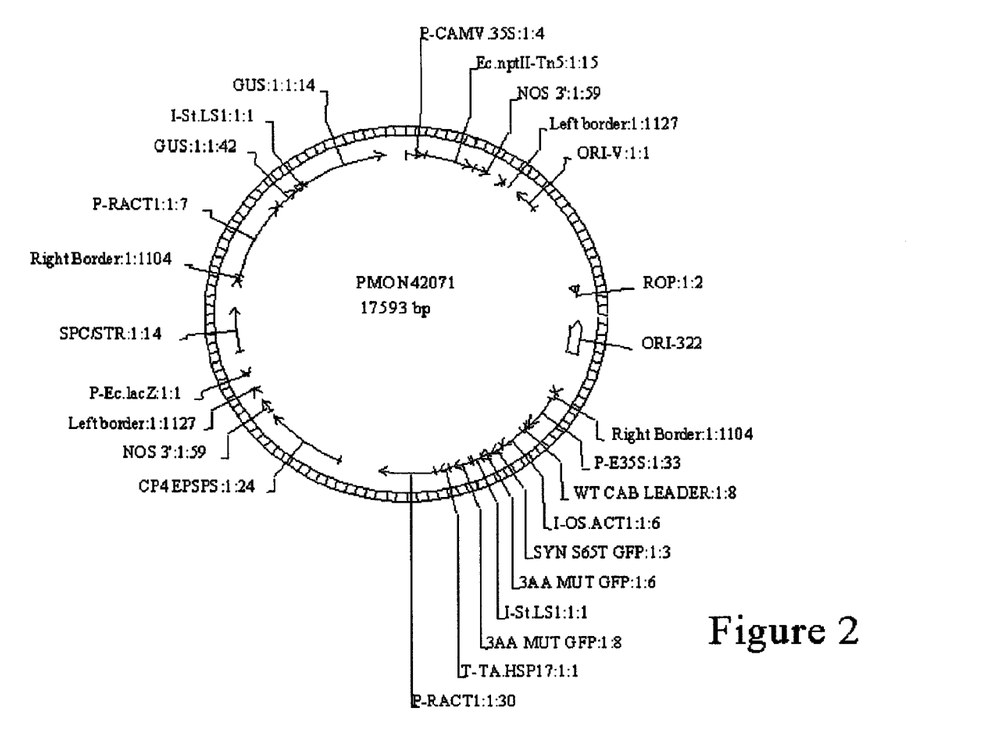
FIG. 2 is a plasmid map of pMON42071.
Figure 3:
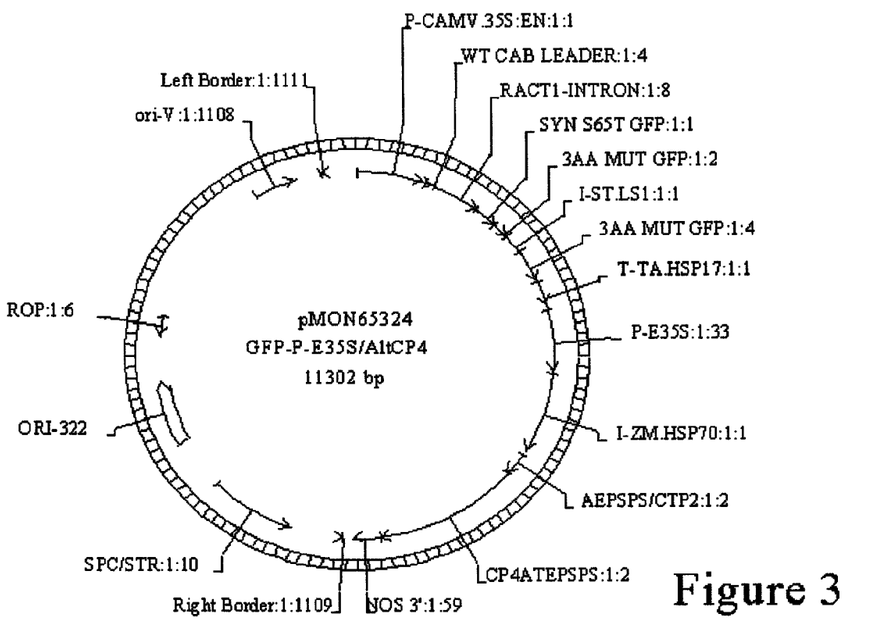
FIG. 3 is a plasmid map of pMON65324.

*Agrobacterium tumefaciens* strain ABI is harbored with the binary vectors pMON30113 (FIG. 1), pMON42071 (FIG. 2), or pMON65324 (FIG. 3). The T-DNA in pMON30113 contains a neomycin phosphotransferase II gene (nptII) as the selectable marker and a green fluorescence protein gene (gfp) screenable marker, both driven by 35S promoter, respectively. pMON42071 has 2 T-DNA, with nptII driven by an e35S promoter and GUS genes by a rice actin promoter on one T-DNA and CP4 driven by a rice actin promoter and gfp genes by an e35S promoter on another. pMON65324 has CP4 and gfp genes each driven by an e35S promoter also on the T-DNA.

Example 2

Preparation of *Agrobacterium*

*Agrobacterium* ABI containing a vector in glycerol stock is streaked out on solid LB medium supplemented with antibiotics kanamycin (50 mg/L), spectinomycin (50 mg/L), streptomycin (50 mg/L) and chloramphenicol (25 mg/L) and incubated at 28° C. for 2 days. Two days before *Agrobacterium* inoculation of the maize immature embryos, one colony or a small loop of *Agrobacterium* from the *Agrobacterium* plate is picked up and inoculated into 25 mL of liquid LB medium supplemented with 100 mg/L of spectinomycin and 50 mg/L of kanamycin in a 250-mL flask. The flask is placed on a shaker at approximately 150 rpm and 26° C. overnight. The *Agrobacterium* culture is then diluted (1 to 5) in the same liquid medium and put back on the shaker. Several hours later, one day before inoculation, the *Agrobacterium* cells are spun down at 3500 rpm for 15 min. The bacterium cell pellet is re-suspended in induction broth with 200 μM of acetosyringone and 50 mg/L spectinomycin and 25 mg/L kanamycin and the cell density was adjusted to 0.2 at $O.D._{660}$. The bacterium cell culture (50 mL in each 250-mL flask) is then put back on the shaker and grown overnight. On the morning of inoculation day, the bacterium cells are spun down and washed with liquid ½MS VI medium (Table 1) supplemented with 200 μM of acetosyringone. After one more spinning, the bacterium cell pellet is re-suspended in ½MS PL medium (Table 1) with 200 μM of acetosyringone (Table 1) and the cell density was adjusted to 1.0 at $O.D._{660}$ for inoculation.

Reagents are commercially available and can be purchased from a number of suppliers (see, for example Sigma Chemical Co., St. Louis, Mo.).

TABLE 1

Media used in this invention[1].

| Component | ½ MS VI | ½ MS PL | Co-culture medium | Induction MS | MSW50 | MS/6B A | MSO D |
|---|---|---|---|---|---|---|---|
| MS salts | 68.5 g/l | 68.5 g/l | 2.2 g/l | 4.4 g/l | 4.4 g/l | 4.4 g/l | 4.4 g/l |
| Sucrose | 20 g/l | 68.6 g/l | 20 g/l | 30 g/l | 30 g/l | 30 g/l | — |
| Maltose | — | — | — | — | — | — | 20 g/l |
| Glucose | 10 g/l | 36 g/l | 10 g/l | — | — | — | 10 g/l |
| 1-Proline | 115 mg/l | 115 mg/l | 115 mg/l | 1.36 g/l | 1.38 g/l | 1.36 g/l | — |
| Casamino Acids | — | — | — | 50 mg/l | 500 mg/l | 50 mg/l | — |
| Glycine | 2 mg/l | 2 mg/l | 2 mg/l | — | 2 mg/l | — | — |
| 1-Asparagine | — | — | — | — | — | — | 150 mg/l |

TABLE 1-continued

Media used in this invention[1].

| Component | ½ MS VI | ½ MS PL | Co-culture medium | Induction MS | MSW50 | MS/6BA | MSO D |
|---|---|---|---|---|---|---|---|
| myo-Inositol | 100 mg/l | 100 mg/l | 100 mg/l | — | 100 mg/l | — | 100 mg/l |
| Nicotinic Acid | 0.5 mg/l | 0.5 mg/l | 0.5 mg/l | 1.3 mg/l | 0.5 mg/l | 1.3 mg/l | 1.3 mg/l |
| Pyridoxine•HCl | 0.5 mg/l | 0.5 mg/l | 0.5 mg/l | 0.25 mg/l | 0.5 mg/l | 0.25 mg/l | 0.25 mg/l |
| Thiamine•HCl | 0.1 mg/l | 0.1 mg/l | 0.6 mg/l | 0.25 mg/l | 0.6 mg/l | 0.25 mg/l | 0.25 mg/l |
| Ca Pantothenate | — | — | — | 0.25 mg/l | — | 0.25 mg/l | 0.25 mg/l |
| 2,4-D | — | — | 3 mg/l | 0.5 mg/l | 0.5 mg/l | — | — |
| Picloram | — | — | — | 2.2 mg/l | — | — | — |
| Silver Nitrate | — | — | 1.7 mg/l | 1.7 mg/l | — | — | — |
| BAP | — | — | — | — | — | 3.5 mg/l | — |

[1]Media ½ MSVI and ½ MSPL were used as liquid. Co-culture medium was solidified with 5.5 mg/l low EEO agarose. All other media were solidified with 7 g/l Phytagar for NPTII selection and with 3 g/l phytagel for glyphosate selection.

Example 3

Explant Preparation

Several genotypes of corn were used in this study. Ears containing immature embryos are harvested approximately 10 days after pollination and kept refrigerated at 4° C. until use (up to 5 days post-harvest). The preferred embryo size for this method of transformation is ~1.0-2.0 mm. This size is usually achieved 10 days after pollination inside the green house with the growth conditions of an average temperature of 87° F., day length of 14 hours with supplemental lighting supplied by GE 1000 Watt High Pressure Sodium lamps.

Example 4

Inoculation

Immature embryos are isolated from surface sterilized ears and directly dropped into the prepared *Agrobacterium* cell suspension in 1.5-mL microcentrifuge tube. The isolation lasts continuously for 15 min. The tube is then set aside for 5 min, which made the inoculation time for individual embryos from 5 to 20 min. After-*Agrobacterium* cell suspension is removed using a fine tipped sterile transfer pipette, the immature embryos are transferred onto the co-culture medium (Table 1). The embryos are placed on the medium with the scutellum side facing up. The embryos are cultured in a dark incubator (23° C.) for approximately 24 h.

Example 5

Selection, Regeneration and Growth of Transformants with Paromomycin Selection

After the co-cultivation, the embryos were transferred onto a modified MS medium (Induction MS, Table 1) supplemented with 500 mg/L carbenicillin and 50, 100, 150 or 200 mg/L paromomycin in Petri dishes (100 mm×25 mm), 20 to 25 embryos per plate. The plates were kept in a dark culture room at 27° C. for approximately 2 weeks. At the end of 2 weeks, each piece of callus cultures from individual embryos was examined under a fluorescence stereomicroscope and the number of callus pieces with well-developed GFP-positive sectors were determined. All the callus pieces were then transferred individually onto the first regeneration medium, the same medium mentioned above except 2,4-D and picloram were replaced by 3.5 mg/L BAP (MS/BAP, Table 1) and the carbenicillin level was dropped to 250 mg/L. The cultures were moved to a culture room with 16-h light/8-h photoperiod and 27° C. After 5-7 days, the callus pieces were transferred onto the second regeneration medium, a hormone-free-MS-based medium (MSOD, Table 1) in Petri dishes (100 mm×25 mm). In another 2 weeks, the callus pieces that had shoots regenerated or were still alive were transferred onto the same hormone-free medium in Phytatrays for further growth. Regenerated plants (R0) when they reached to the top of Phytatrays and had one or more healthy roots were moved to soil in peat pots in a growth chamber. In 7 to 10 days, they were transplanted into 12-in pots and moved to greenhouse with conditions for normal corn plant growth. The plants were either self-pollinated or crossed with wild-type plants.

Seed Set and Transgene Segregation in R1 Generation:

Immature ears from some of the R0 plants were harvested at different times after pollination. The immature embryos from all or some of the kernels were isolated and cultured on MSOD medium supplemented with 200 mg/L paromomycin. The embryos were examined under the fluorescence microscope to determine the number of embryos with GFP expression. In approximately 7 to 10 days, the number of embryos germinated to seedlings was also determined. Other plants were grown to maturity and seeds were harvested from individual plants.

Development of Transformants:

Almost all the embryos inoculated and co-cultured with *Agrobacterium* for one day showed excellent GFP gene transient expression, which was demonstrated by a great number of single-celled GFP-positive spots on each embryo. The embryos were transferred after one day co-culture onto the selective callus induction medium, a modified MS medium (Induction MS, Table 1) supplemented with 500 mg/L carbenicillin and 50, 100, 150 or 200 mg/L paromomycin. The cultures were examined periodically for the development of GFP-positive sectors. It was observed that most of the GFP-positive spots resulting from the transient expression disappeared within 3-4 days. On the fourth or fifth day, small multiple-celled GFP-positive spots started to emerge on some of the embryos. Those spots gradually developed into GFP-positive sectors that were easily identified under the fluorescence microscope. Some of the embryos could form more than one GFP-positive sector. In two weeks, one fifth to one third of the callus pieces (one callus piece from one embryo) in different experiments showed well-developed GFP-positive sectors. Once the callus pieces were transferred onto the regeneration medium, some of the GFP-positive sectors started to regenerate into shoots. Usually roots would not develop until they had been on the regeneration medium for at least 3 weeks, that is when they were already in Phytatrays.

Some of the plantlets were big enough to be moved to soil after growing in Phytatrays for 2 to 3 weeks (7 to 8 weeks after inoculation). It might take another 2 to 3 weeks to move all the plantlets to soil. Before the plantlets were planted in soil, they were examined under the fluorescence microscope again. Based on all the transgenic events moved to soil in five experiments, approximately 48% of the events had one GFP-positive plant, 52% had 2 to 8 plants.

Transformation Frequency:

One fifth to one third of inoculated embryos developed to callus pieces with GFP-positive sector(s) after being cultured on the callus induction medium with paromomycin. However, it appeared that majority of them were not able to regenerate to plants. Some of them regenerated into small shoots on the regeneration medium but did not grow further. That could be caused by low expression of the transgene or other unknown reasons. At the end, 2 to 5% of transformation efficiencies were achieved based on the number events with GFP-positive plants moved to soil.

Elimination of Non-Transformed Escapes:

In our experiments, it only took 7 to 10 weeks from inoculation to R0 transgenic plants moved to soil. The reduction of overall selection time could make it easier for non-transformed tissue to survive and eventually regenerate to plants if selection stringency is not properly modified, which was reflected in our early experiments. For example, in two experiments, 100 mg/L paromomycin was used at each stage of selection. The level of selection was apparently not high enough, because only 41 and 33%, respectively, of the plants survived the selection and moved to soil were GFP-positive. This high level of escape rate was not acceptable practically and also suggested that the selection stringency should be adjusted. Two approaches were tested to eliminate the non-transformants: 1) increased paromomycin level at each stage, but kept the same; 2) kept the paromomycin at 100 mg/L in early stages, but increased it to 200 mg/L at the last stage of selection (in Phytatrays). To test the first approach, three levels of paromomycin (100, 150 and 200 mg/L) were compared. The results showed in Table 2 suggested that as the paromomycin level in medium increased from 100 to 150 to 200 mg/L, the proportion of GFP-positive plants also increased from 67% at 100 mg/L level to 75% at 150 mg/L and to 83% at 200 mg/L. In Experiment 3370, all the tissue were selected on medium containing 100 mg/L paromomycin, but the paromomycin level was increased to 200 mg/L at the last stage of selection (in Phytatrays). Among the plants moved to soil in this experiment 72% were GFP-positive, which was much higher than in Experiments 3307 and 3324. These results suggest that the escape rate could be significantly reduced by increasing the selection stringency starting from beginning or at the last stage of selection, although more study is necessary to find an optimal selection regime.

TABLE 2

Effect of selection stringency on escape rate.

| | | | # plants to soil | |
|---|---|---|---|---|
| Exp-Treat # | Selection regime[a] | Total | GFP+ | GFP− |
| 3307 | P100 | 61 | 25 (41%) | 36 (59%) |
| 3324 | P100 | 45 | 15 (33%) | 30 (67%) |
| 3368-1 | P100 | 6 | 4 (67%) | 2 (33%) |
| 3368-2 | P150 | 12 | 9 (75%) | 3 (25%) |

TABLE 2-continued

Effect of selection stringency on escape rate.

| | | | # plants to soil | |
|---|---|---|---|---|
| Exp-Treat # | Selection regime[a] | Total | GFP+ | GFP− |
| 3368-3 | P200 | 30 | 25 (83%) | 5 (17%) |
| 3370 | P100 → P200 | 25 | 18 (72%) | 7 (28%) |

[a]P100, P150 and P200 mean 100, 150 and 200 mg/L paromomycin, respectively. In all the experiments and treatments, the selection level was maintained the same from the callus induction to the last stage of regeneration except in Experiment 3370. In Experiment 3370, the cultures were selected on medium containing 100 mg/L paromomycin until the last stage of regeneration (in Phytatrays) in which the paromomycin level was raised to 200 mg/L.

Using this system, transformed R0 plants were transferred to soil approximately two months after the explants were inoculated with *Agrobacterium*. Because the amount of tissue culture manipulation was significantly reduced, the time of production of high quality transgenic maize plants was reduced, and maize transformation was much less tedious. It should also work for other explant materials besides immature embryos.

Example 6

Selection, Regeneration and Growth of Transformants Through NPTII Selection

Immature embryos from a different corn line were inoculated and co-cultivated with *Agrobacterium* ABI::pMON30113 as described earlier. The embryos were then transferred onto a modified MS medium (MSW50, Table 1) supplemented with 100 or 200 mg/L paromomycin and 500 mg/L carbenicillin to inhibit *Agrobacterium* in Petri dishes (100 mm×25 mm). The cultures were incubated in a dark culture room at 27° C. for 2-3 weeks. All the callus pieces were then transferred individually onto the first regeneration medium (MS/6BA, Table 1) supplemented with the same levels of paromomycin. The cultures were grown on this medium and in a culture room with 16-h light/8-h dark photoperiod and 27° C. for 5-7 days. They were then transferred onto the second regeneration medium (MSOD, Table 1) in Petri dishes (100 mm×25 mm) for approximately 2 weeks. All the callus pieces with regenerating shoots and living tissue were transferred onto the same medium contained in Phytatrays for shoots to grow further before being moved to soil. It took 2-4 weeks. The regeneration media (MS6BA and MSOD) were all supplemented with 250 mg/L carbenicillin and 100 or 200 mg/L paromomycin.

Transformation Frequency Through NPTII Selection:

In 2 to 3 weeks, a number of callus pieces developed sectors expressing GFP. In two experiments, the number of callus pieces developed GFP-expressing sectors varied significantly. It was close to 24% in one experiment, and 61.5% in another. Most of the sectors were apparently non-regenerable and only a small number of them regenerated into small shoots. Eventually, similar to the first corn line, 2.4 and 3.3% of transformation efficiency were achieved in these two experiments, respectively.

Example 7

Selection, Regeneration and Growth of Transformants Through Glyphosate Selection Embryos inoculated and co-cultured with *Agrobacterium* ABI::pMON42071 or pMON65324 were selected on the callus induction medium (MSW50, Table 1) supplemented with 0.1 or 0.25 mM glyphosate and 500 mg/L carbenicillin for approximately 3 weeks. All the callus pieces developed from individual embryos were regenerated the same way and under the same conditions as described in last section for the NPTII selection, except the MS6BA and MSOD media were supplemented with 250 mg/L carbenicillin and 0.1 or 0.25 mM glyphosate instead of paromomycin.

Transformation Frequency Through Glyphosate Selection:

Five experiments were conducted with either ABI::pMON42071 or ABI::pMON65324. Inoculated immature embryos were selected on the callus induction medium, MSW50 supplemented with 0.1 or 0.25 mM glyphosate for approximately 3 weeks. Almost all the embryos were able to develop some callus tissue, and they were all moved onto the regeneration medium supplemented with 0.1 or 0.25 mM glyphosate for plant regeneration and further selection. The transformation efficiency varied from experiment to experiment with a range from 0.5 to 3.1%. Unlike in the experiments with NPTII selection, all regenerated plants from the glyphosate selection experiments were GFP-positive.

Example 8

Selection Temperature

This example describes the use of increased incubation temperature during the selection process. The usual temperature is 27° C. Immature embryos were transformed as described above and selected with glyphosate as in Example 7, with the exception of the Induction MS containing 4.4 g/L MS salts, 30 g/L sucrose, 1.38 g/L proline, 500 mg/L casamino acids, 100 mg/L inositol, 0.5 mg/L nicotinic acid, 0.5 mg/L pyridoxine, 0.6 mg/L thiamine, 0.5 mg/L 2,4-D, 1.7 mg/L silver nitrate and 20 mg/L BAP. During the first two weeks of selection, temperatures of 27° C., 30° C., 32° C. and 34° C. were compared. After two weeks, the temperature was reduced to 27° C. for the final week of selection. There was also the addition of a rooting media (MSOD with 0.75 mg/L IBA and 0.5 mg/L NAA and 0.1 mM glyphosate) during the final regeneration step. With an average of 5 experiments, 27° C. gave a transformation frequency of 3.6%, 30° C. was 6.7%, 32° C. was 6.9%, and 34° C. was 8.4% (Table 3). The higher temperatures of 32° C. and 34° C. gave an increased number of abnormal albino or striped events. The earlier transformation frequencies are for normal events. Experiments were also done that compared 27° C. with 30° C. A direct comparison of the two temperatures during the same experiment had a transformation frequency of 3.4% for 27° C. and 9.9% for 30° C. Over a large number of transformations at 27° C., transformation frequency averaged 5.5%. At 30° C., transformation frequency averaged 15%. Overall, the increase in temperature during selection increased the transformation frequency by about twofold.

TABLE 3

Effect of Callus Induction Temp. on TF of the CP4 Agro-mediated Tfn System

| Exp. # | Trt. Temp | # Explants | # Normal Events to Soil | # Albino or Striped Events | TF % (all events) | TF % (normal events) |
|---|---|---|---|---|---|---|
| 4915 | 27 C. | 261 | 19 | 1 | 7.7 | 7.3 |
|  | 30 C. | 261 | 29 | 1 | 11.5 | 11.1 |
|  | 32 C. | 261 | 22 | 0 | 8.4 | 8.4 |
|  | 34 C. | 259 | 18 | 2 | 7.7 | 6.9 |
| 4921 | 27 C. | 350 | 0 | 0 | 0.0 | 0.0 |
|  | 30 C. | 348 | 18 | 1 | 5.5 | 5.2 |
|  | 32 C. | 337 | 18 | 1 | 5.6 | 5.3 |
|  | 34 C. | 344 | 19 | 1 | 5.8 | 5.5 |
| 4922 | 27 C. | 220 | 7 | 0 | 3.2 | 3.2 |
|  | 30 C. | 220 | 6 | 0 | 2.7 | 2.7 |
|  | 32 C. | 220 | 6 | 1 | 3.2 | 2.7 |
|  | 34 C. | 220 | 7 | 2 | 4.1 | 3.2 |
| 4929 | 27 C. | 369 | 13 | 0 | 3.5 | 3.5 |
|  | 30 C. | 369 | 29 | 4 | 8.9 | 7.9 |
|  | 32 C. | 369 | 24 | 2 | 7.0 | 6.5 |
|  | 34 C. | 369 | 47 | 5 | 14.1 | 12.7 |
| 4931 | 27 C. | 344 | 16 | 1 | 4.9 | 4.7 |
|  | 30 C. | 347 | 26 | 1 | 7.8 | 7.5 |
|  | 32 C. | 342 | 36 | 2 | 11.1 | 10.5 |
|  | 34 C. | 342 | 38 | 3 | 12.0 | 11.1 |
| Total | 27 C. | 1544 | 55 | 2 | 3.7 | 3.6 |
|  | 30 C. | 1545 | 108 | 1 | 7.4 | 6.7 |
|  | 32 C. | 1529 | 106 | 6 | 7.3 | 6.9 |
|  | 34 C. | 1534 | 129 | 13 | 9.3 | 8.4 |

Example 9

Detection of GFP Expression

Inoculated immature embryos, callus tissue developed from the embryos, and regenerated shoots were examined periodically under a Leica MZ80 dissecting microscope equipped with a filter set (HQ480/40 excitation, HQ535/50 emission and Q505LP dichroic mirror), especially at one day after inoculation and the end of each selection and regeneration phases. All the R0 plants were also examined for the GFP expression before being moved to soil.

Seed Set and Transgene Segregation in R1 Generation:

Immature ears of some of the R0 plants from NPTII selection were harvested at different times after pollination. The immature embryos from all or some of the kernels were isolated and cultured on MSOD medium supplemented with 200 mg/L paromomycin. The embryos were examined under the fluorescence microscope to determine the number of embryos with GFP expression. In approximately 7 to 10 days, the number of embryos germinated to seedlings was also determined.

The invention claimed is:

1. A method for increasing the transformation efficiency of a maize transformation process comprising limiting the anaerobiosis effect during the inoculation of *Agrobacterium* to the transformable maize tissue explant by
   (i) isolating a maize explant directly into inoculation medium containing *Agrobacterium* and removing the maize explant from the inoculation medium within 20 minutes;
   (ii) spotting a maize explant with an *Agrobacterium* solution wherein the maize explant is contacted by the *Agrobacterium* solution for 5 to 60 minutes; or
   (iii) contacting the maize explant with filter paper comprising a solution of *Agrobacterium* for 5 to 60 minutes;
   thereby obtaining transformed maize tissue with an increased transformation efficiency;
   wherein the transformed maize tissue is cultured in a selection medium at a temperature of from 30° C. to about 34° C. during the first two weeks of selection,
   and then cultured in a selection medium at a temperature of about 27° C. during the final week of selection.

2. The method of claim 1, comprising culturing transformed maize tissue at a temperature of about 32° C. during the first two weeks of selection.

3. The method of claim 1, wherein the period of time in the selection media is between about 7 days and about 28 days.

4. The method of claim 1, wherein the selection temperature during the first two weeks of selection is maintained for a period of time between about 7 days and about 14 days.

5. The method of claim 1, wherein the transformable maize tissue explant is an immature embryo.

6. The method of claim 1, wherein the selection is performed in a single vessel without replacing or replenishing the selection media during the selection period.

7. The method of claim 1, wherein the selection compound is an herbicide.

8. The method of claim 7, wherein the herbicide is selected from the group consisting of glyphosate, bialaphos, phosphinothricin or Basta.

* * * * *